US008845712B2

(12) United States Patent
Irwin et al.

(10) Patent No.: US 8,845,712 B2
(45) Date of Patent: Sep. 30, 2014

(54) PLEATED DEPLOYMENT SHEATH

(75) Inventors: Craig W. Irwin, Parks, AZ (US); James D. Silverman, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 1441 days.

(21) Appl. No.: 12/014,536

(22) Filed: Jan. 15, 2008

(65) Prior Publication Data
US 2009/0182411 A1 Jul. 16, 2009

(51) Int. Cl.
*A61F 2/06* (2013.01)
*A61F 2/962* (2013.01)
*A61F 2/97* (2013.01)

(52) U.S. Cl.
CPC .. *A61F 2/962* (2013.01); *A61F 2/97* (2013.01)
USPC ........................................ 623/1.12; 623/1.11

(58) Field of Classification Search
CPC ........... A61F 2/95; A61F 2/958; A61F 2/962; A61F 2/97; A61F 2/966; A61F 2002/9511; A61F 2002/9583; A61F 2002/9505; A61F 2002/9665; A61M 2025/0024; A61M 2025/0175; A61M 2025/0183; A61M 2025/0188
USPC ........................ 623/1.11, 1.12, 1.23; 606/108; 604/164.01, 167.01, 103.05–103.08, 604/164.03, 271, 167.03, 264
See application file for complete search history.

(56) References Cited

U.S. PATENT DOCUMENTS

| | | | |
|---|---|---|---|
| 3,225,129 A | 12/1965 | Taylor et al. | |
| 4,141,364 A | 2/1979 | Schultze | |
| 4,411,655 A * | 10/1983 | Schreck | 604/165.01 |
| 4,569,347 A * | 2/1986 | Frisbie | 606/108 |
| 4,601,713 A * | 7/1986 | Fuqua | 604/514 |
| 4,655,771 A | 4/1987 | Wallsten | |
| 4,732,152 A | 3/1988 | Wallsten et al. | |
| 4,738,666 A * | 4/1988 | Fuqua | 604/514 |
| 4,848,343 A | 7/1989 | Wallsten et al. | |
| 4,875,480 A | 10/1989 | Imbert | |
| 4,921,479 A * | 5/1990 | Grayzel | 604/509 |
| 5,066,298 A * | 11/1991 | Hess | 606/194 |
| 5,139,511 A * | 8/1992 | Gill et al. | 606/198 |
| 5,171,262 A | 12/1992 | MacGregor | |
| 5,171,305 A * | 12/1992 | Schickling et al. | 604/271 |
| 5,176,659 A * | 1/1993 | Mancini | 604/523 |
| 5,211,654 A * | 5/1993 | Kaltenbach | 606/191 |
| 5,234,425 A | 8/1993 | Fogarty et al. | |
| 5,318,588 A | 6/1994 | Horzewski et al. | |

(Continued)

FOREIGN PATENT DOCUMENTS

EP 163 525 12/1985
EP 0682922 4/1994

(Continued)

*Primary Examiner* — Dianne Dornbusch
(74) *Attorney, Agent, or Firm* — David J. Johns

(57) ABSTRACT

A deployment sheath for medical devices is provided that includes one or more pleats in its pre-deployment state that are allowed to open during deployment so as to facilitate easier device deployment and sheath removal. Preferably, the sheath is removed by everting it over itself during the delivery process. By orienting the pleats along the length of the sheath, preferably helically around the sheath, the sheath undergoes a predictable enlargement during deployment so as to relieve friction of the everted sheath sliding along itself during deployment. This allows the sheath to be removed with less tension than previous everting sheath constructions and assures more accurate device placement in a patient.

19 Claims, 9 Drawing Sheets

(56) References Cited

U.S. PATENT DOCUMENTS

| | | | |
|---|---|---|---|
| 5,328,469 A | 7/1994 | Coletti | |
| 5,352,236 A * | 10/1994 | Jung et al. | 606/194 |
| 5,364,345 A | 11/1994 | Lowery et al. | |
| 5,382,399 A | 1/1995 | Moret de Rocheprise et al. | |
| 5,395,349 A | 3/1995 | Quiachon et al. | |
| 5,405,377 A | 4/1995 | Cragg | |
| 5,445,646 A * | 8/1995 | Euteneuer et al. | 606/198 |
| 5,447,503 A * | 9/1995 | Miller | 604/528 |
| 5,458,573 A | 10/1995 | Summers | |
| 5,464,419 A * | 11/1995 | Glastra | 606/194 |
| 5,476,508 A | 12/1995 | Amstrup | |
| 5,571,135 A | 11/1996 | Fraser et al. | |
| 5,641,373 A | 6/1997 | Shannon et al. | |
| 5,653,697 A * | 8/1997 | Quiachon et al. | 604/528 |
| 5,662,703 A * | 9/1997 | Yurek et al. | 623/1.12 |
| 5,690,644 A | 11/1997 | Yurek et al. | |
| 5,762,604 A * | 6/1998 | Kieturakis | 600/115 |
| 5,789,047 A | 8/1998 | Sasaki et al. | |
| 5,800,456 A | 9/1998 | Maeda et al. | |
| 5,824,041 A | 10/1998 | Lenker et al. | |
| 5,833,699 A | 11/1998 | Chuter | |
| 5,868,707 A * | 2/1999 | Williams et al. | 604/103 |
| 5,893,868 A * | 4/1999 | Hanson et al. | 623/1.11 |
| 5,993,427 A | 11/1999 | Rolland et al. | |
| 5,997,508 A * | 12/1999 | Lunn et al. | 604/164.08 |
| 6,025,044 A | 2/2000 | Campbell et al. | |
| 6,039,721 A * | 3/2000 | Johnson et al. | 604/508 |
| 6,042,605 A | 3/2000 | Martin et al. | |
| 6,059,813 A * | 5/2000 | Vrba et al. | 606/198 |
| 6,110,146 A * | 8/2000 | Berthiaume et al. | 604/160 |
| 6,126,685 A | 10/2000 | Lenker et al. | |
| 6,174,328 B1 | 1/2001 | Cragg | |
| 6,238,410 B1 | 5/2001 | Vrba et al. | |
| 6,254,628 B1 * | 7/2001 | Wallace et al. | 623/1.12 |
| 6,280,412 B1 * | 8/2001 | Pederson et al. | 604/103.07 |
| 6,352,561 B1 * | 3/2002 | Leopold et al. | 623/1.23 |
| 6,371,980 B1 * | 4/2002 | Rudakov et al. | 623/1.12 |
| 6,387,118 B1 * | 5/2002 | Hanson | 623/1.11 |
| 6,432,130 B1 * | 8/2002 | Hanson | 623/1.11 |
| 6,447,540 B1 * | 9/2002 | Fontaine et al. | 623/1.12 |
| 6,468,243 B1 | 10/2002 | Miyagawa et al. | |
| 6,544,278 B1 | 4/2003 | Vrba et al. | |
| 6,547,813 B2 * | 4/2003 | Stiger et al. | 623/1.11 |
| 6,607,552 B1 * | 8/2003 | Hanson | 623/1.11 |
| 6,652,492 B1 * | 11/2003 | Bell et al. | 604/167.01 |
| 6,939,327 B2 * | 9/2005 | Hall et al. | 604/164.05 |
| 6,942,682 B2 | 9/2005 | Vrba et al. | |
| 7,105,013 B2 * | 9/2006 | Durcan | 623/1.11 |
| 7,534,250 B2 * | 5/2009 | Schaeffer et al. | 606/191 |
| 7,625,337 B2 * | 12/2009 | Campbell et al. | 600/156 |
| 7,766,820 B2 * | 8/2010 | Core | 600/140 |
| 7,780,630 B2 * | 8/2010 | Jenson et al. | 604/103.14 |
| 7,780,692 B2 * | 8/2010 | Nance et al. | 606/198 |
| 8,435,282 B2 | 5/2013 | Silverman | |
| 2002/0016607 A1 * | 2/2002 | Bonadio et al. | 606/192 |
| 2002/0099431 A1 * | 7/2002 | Armstrong et al. | 623/1.11 |
| 2002/0116045 A1 | 8/2002 | Eidenschink | |
| 2003/0088309 A1 | 5/2003 | Iwasaka et al. | |
| 2003/0176909 A1 | 9/2003 | Kusleika | |
| 2003/0208223 A1 | 11/2003 | Kleiner | |
| 2004/0044359 A1 * | 3/2004 | Renati et al. | 606/200 |
| 2004/0087968 A1 * | 5/2004 | Core | 606/108 |
| 2004/0143272 A1 | 7/2004 | Cully et al. | |
| 2004/0143315 A1 | 7/2004 | Bruun et al. | |
| 2005/0222576 A1 * | 10/2005 | Kick et al. | 606/104 |
| 2005/0228479 A1 | 10/2005 | Pavcnik et al. | |
| 2005/0245892 A1 * | 11/2005 | Elkins et al. | 604/508 |
| 2005/0246008 A1 | 11/2005 | Hogendijk et al. | |
| 2005/0267568 A1 | 12/2005 | Berez et al. | |
| 2006/0025844 A1 | 2/2006 | Majercak et al. | |
| 2006/0030923 A1 * | 2/2006 | Gunderson | 623/1.11 |
| 2006/0041302 A1 * | 2/2006 | Malewicz | 623/1.11 |
| 2006/0074476 A1 | 4/2006 | Holman et al. | |
| 2006/0155357 A1 | 7/2006 | Melsheimer | |
| 2006/0184225 A1 | 8/2006 | Pryor | |
| 2006/0184226 A1 | 8/2006 | Austin | |
| 2006/0200221 A1 * | 9/2006 | Malewicz | 623/1.11 |
| 2006/0276872 A1 | 12/2006 | Arbefeuille et al. | |
| 2006/0282152 A1 | 12/2006 | Beyerlein et al. | |
| 2006/0287671 A1 * | 12/2006 | Renati et al. | 606/200 |
| 2007/0055338 A1 | 3/2007 | Dorn | |
| 2007/0198077 A1 * | 8/2007 | Cully et al. | 623/1.12 |
| 2008/0097301 A1 | 4/2008 | Alpini et al. | |
| 2008/0312733 A1 | 12/2008 | Jordan | |
| 2011/0144739 A1 | 6/2011 | Cattaneo | |

FOREIGN PATENT DOCUMENTS

| | | |
|---|---|---|
| WO | 97/02791 | 1/1997 |
| WO | 98/33454 | 8/1998 |
| WO | 00/74584 | 12/2000 |
| WO | 02/38084 | 5/2002 |
| WO | 03/045284 | 6/2003 |
| WO | 2009/002827 | 12/2008 |
| WO | 2010/015370 | 2/2010 |
| WO | 2010/034453 | 4/2010 |

* cited by examiner

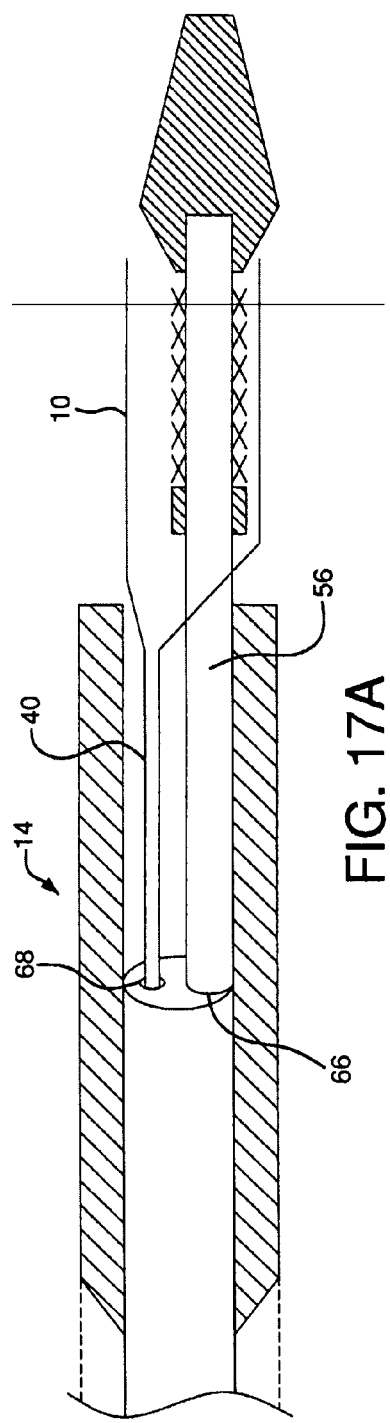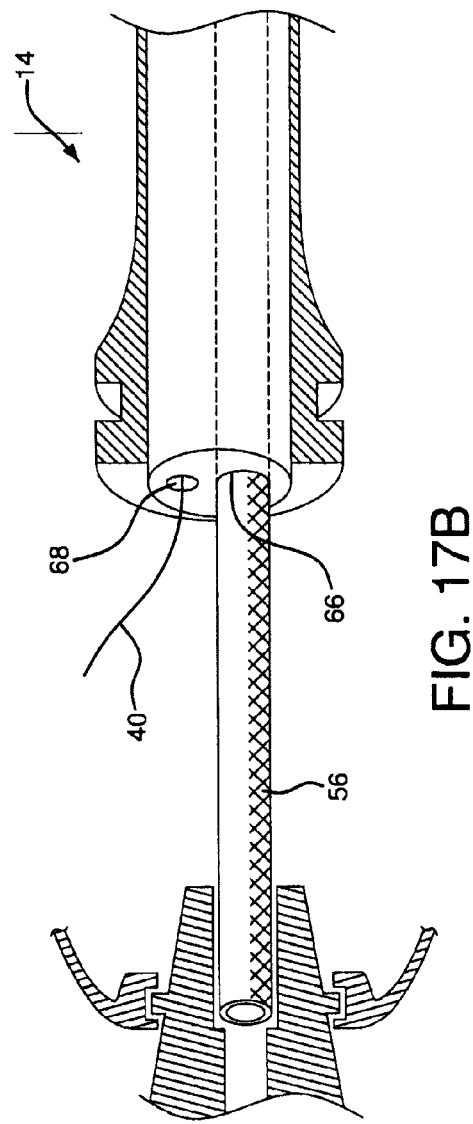

PLEATED DEPLOYMENT SHEATH

BACKGROUND OF THE INVENTION

1. Field of the Invention

The present invention relates to apparatus used to position and deploy medical diagnostic and treatment devices in a body.

2. Discussion of the Related Art

A growing number of medical diagnostic and treatment devices are being developed that are remotely used to assess and/or treat patients, typically being guided to a target site using imagining technology such as fluoroscopes or ultrasound. Such devices include stents, stent-grafts, balloons, blood filters, occluders, probes, valves, electronic leads, orthopedic devices, etc. Usually these devices are mounted near the end of a catheter or guidewire and are remotely steered to the targeted site. Radiopaque markers or similar indicia are often used to allow the medical staff to exactly position the medical device using the imagining technology.

Once properly positioned, the medical staff will then carry out the procedure and/or deploy the necessary device or devices. Since most of these procedures, such as interventional treatment of occlusions or aneurysms, require exact placement of a treatment device, it is important that the device deploys in the same position where it had been initially placed. For instance, in treating aortic aneurysms with a stent-graft, physicians expect displacement of the device of less than 5 mm following deployment. Any greater displacement may result in endoleaks, blocked side vessels, or other complications requiring otherwise unnecessary further treatments or even risky conversion to open surgery.

Not surprisingly, numerous apparatus have been proposed to facilitate the placement of such devices. Originally self-expanding devices were simply drawn or stuffed into a catheter tube and then pushed out at the treatment site. Exact placement using this method can prove somewhat elusive, with the medical staff often required to deploy and retract the device repeatedly before the correct orientation is achieved.

More exacting deployment methods have since been developed, such as employing various constraining cords, e.g., those described in U.S. Pat. No. 6,042,605 to Martin et al., or implantable constraining sheaths, e.g., those described in U.S. Pat. No. 6,352,561 to Leopold et al.

A similar concept to the original catheter tube constraint is to use a thin sheath of material that is pulled back over the treatment device while holding the device in place. One advantage of this concept is that the device and thin sheath can take up considerably less space than housing a device within a relatively bulky catheter tube. The thin sheaths also can provide greater flexibility over much stiffer catheter tube materials. Such compactness and flexibility are highly desirable as physicians try to reach tighter treatment sites through smaller and more tortuous vessels. Unfortunately, this method can put considerable strain on a self-expanding device, which is exerting pressure against the constraining sheath throughout the deployment process. The resulting friction between the device and the sheath often requires application of considerable tensile force to remove the sheath, making ultimate exact positioning much more difficult, as well as possibly damaging the treatment device in the process of sheath removal.

One deployment method to limit such effects is to employ a thin sheath of material that is everted over itself, so that the constraining sheath rubs only against itself while it is being pulled back over a self-expanding device. In other words, a sheath of a given diameter is everted back over itself and then pulled down the length of the sheath through the deployment procedure. Variations on this concept are described in, for instance, U.S. Pat. No. 4,732,152 to Wallsten, U.S. Pat. No. 5,571,135 to Fraser et al., U.S. Pat. No. 6,942,682 to Vrba et al., and US Application 2006/0025844 to Majercak et al., and US Patent Application 2006/0030923 to Gunderson. With sufficiently thin and strong sheath materials, these methods offer the prospect of compactness with less strain placed on the treatment device and perhaps more precise device placement.

While everting sheaths address some of the complications seen with non-everting sheaths, they still can require considerable tension in order to pull the sheath over itself and the self-expanding device during deployment, resulting mainly from the friction of everted portion of the sheath rubbing against the non-everted portion of the sheath while the sheath is being removed. These concerns are compounded with longer device lengths and more robust self-expanding devices that exert greater outward pressures. The greater the tension needed to evert and remove the sheath, the more demanding it is for the medical staff to remove the sheath while trying to hold the apparatus in its exact position during deployment. Increased deployment tensions also require more substantial sheath constructions so as to avoid sheath and deployment line breakage during deployment. It is believed that these deficiencies of everting sheaths may have limited practical applications for such deployment methods.

Accordingly, it would be desirable to develop a deployment apparatus that retains many of the benefits of everting sheath deployment while allowing for lower deployment tensions and more exact device placement.

SUMMARY OF THE INVENTION

The present invention is directed to a deployment sheath for medical devices that includes one or more pleats in its pre-deployment state that are allowed to open during deployment so as to facilitate easier sheath removal. Preferably, the sheath is deployed by everting it over itself during the delivery process. By orienting the pleats along the length of the sheath, preferably helically around the sheath, the sheath undergoes a predictable enlargement during device deployment so as to relieve friction of the everted sheath sliding along itself during deployment. This allows the sheath to be removed with considerably less tension than previous everting sheath constructions and assures more accurate device placement in a patient.

In one embodiment of the present invention, the sheath may be used to deliver an endoprosthesis. The sheath may be tubular in construct and includes at least one pleat oriented along at least a portion of its length, preferably helically along its length. The pleat may incorporate a material or other feature that resists folding and tensile strain, such as a polyimide, to aid in creating and maintaining the pleat form and orientation.

In a further embodiment of the present invention, the sheath may be used to deploy a medical device with the sheath at least partially everted over itself to form an interior segment and an exterior segment in the pre-deployed configuration. At least one pleat is provided along at least a portion of the interior segment, again preferably in a helical orientation. When deployment occurs by applying tension to the exterior segment of the sheath, the interior segment progressively reorients itself into the exterior segment with the pleat progressively opening as the sheath everts. This un-pleating of the sheath as it becomes the exterior segment allows the exterior segment to be of sufficiently greater diameter than the pleated interior segment so as to reduce frictional contact between the interior segment and the exterior segment during deployment.

By minimizing the frictional contact of the sheath upon itself, it has been determined that the sheath can be removed with considerably less applied tension than has been required in prior sheath containment apparatus. Once again, it is preferred that the sheath incorporates a material or other feature that is resistant to folding and tensile strain to aid in pleat formation and maintenance.

The deployment apparatus of the present invention may be used to deploy a wide variety of devices to diagnose and/or treat patients. Such devices may include stents, stent-grafts, balloons, blood filters, occluders, probes, valves, electronic leads (e.g., pacing or defibulator leads), orthopedic devices, etc.

The deployment apparatus of the present invention may be modified to address many different device delivery and deployment needs. For instance, the number of pleats, the orientation of the pleats, the size and spacing of the pleats, pleat pitch, etc., can be adjusted to allow devices to deploy in different manners. Additionally, the sheaths of the present invention can be mounted in a variety of ways on devices to accommodate different deployment requirements, such as allowing a device to deploy off a catheter hub-to-tip, or tip-to-hub, or from a mid-point of a device outward in both directions.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 17A is a partially cut-way perspective view of a distal portion of a catheter utilizing a sheath of the present invention, showing still another embodiment of apparatus to remove the sheath;

FIG. 17B is a partially cut-way perspective view of a proximal portion the catheter shaft of FIG. 17A;

DETAILED DESCRIPTION OF THE ILLUSTRATED EMBODIMENTS

Reference will now be made in detail to an embodiment of the present invention, example of which is illustrated in the accompanying drawings.

The present invention employs a pleated deployment sheath for medical device containment and delivery, preferably for use with everting sheath delivery. One or more pleats are pre-formed into the sheath in its pre-deployment state and are allowed to open during deployment so as to facilitate easier sheath removal. By orienting the pleats longitudinally along the length of the sheath, preferably helically around the sheath, the sheath undergoes a predictable enlargement during deployment and thus relieves friction of the everted sheath sliding along itself during deployment. This allows the sheath to be removed with considerably less tension than previous everting sheath constructions and assures more accurate device placement in a patient.

Figure 1:
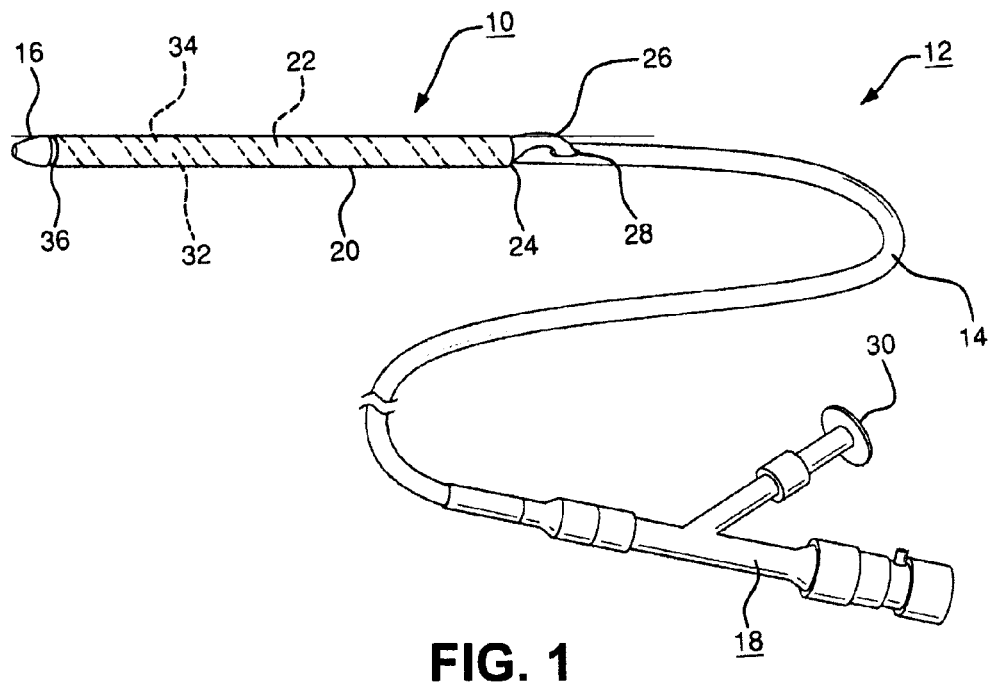
FIG. 1 is a plan view of one embodiment of a medical device deployment system employing a pleated sheath of the present invention mounted near a distal end of a delivery catheter.

Shown in FIG. 1 is one embodiment of a pleated sheath 10 of the present invention mounted near the end of a medical device deployment system 12. The deployment system comprises a catheter shaft 14 extending from a distal olive 16 to a control hub 18. A medical device, such as a stent, stent-graft, balloon, blood filter, occluder, probe, valves, etc., may be contained in the sheath 10 to be deployed at a treatment site within a patient's body. In the embodiment shown, the sheath 10 is everted over itself to form two layers, an exterior segment 20 which, in this embodiment, completely covers an interior segment 22. The exterior segment is split at its proximal end 24 to form a deployment line 26 that is fed into the catheter shaft through opening 28. The deployment line 26 is operatively connected to a deployment knob 30 on the hub 18.

The sheath 10 may be formed from any material that is sufficiently strong both to constrain the device to be delivered and to withstand the tension of the removal process. It is desirable that the sheath 10 also be as thin and lubricious as possible so as to maintain a small device delivery profile and to facilitate the removal process. Since the sheath 10 is placed temporarily deep within a patient during delivery and deployment, it is likewise desirable that the sheath be formed from a biocompatible material. As is explained in greater detail below, suitable sheath materials may include: polytetrafluoroethylene (PTFE); expanded PTFE (ePTFE); fluorinated ethylene propylene (FEP), polyethylene teraphthalate (PET), nylon, polyurethane, polypropylene, polyester, etc.

In this embodiment of the present invention, the interior segment 22 includes a helical pleat 32 extending fully along its length. The pleat 32 comprises a fold in the material of the sheath that reduces the interior segment 22 of the sheath to a diameter smaller than the diameter of the exterior segment 20. In order to aid in forming and maintaining the pleat 32, a reinforcing material 34 may be layered over or otherwise attached to the sheath. Preferably such material is fold-resistant so that the pleat more readily holds its correct orientation along its entire length during the folding process and through sheath deployment. Suitable reinforcing materials may include: one or more strips of polymer material, such as polyimide, polyethylene teraphthalate (PET), nylon, polyurethane, or similar material, adhered to the sheath; a coating applied to the strip that hardens to provide the desired properties, such as providing sufficient stiffness/Young's Modulus and thickness to resist folding for a given helical pitch, pleat width, and effective diameter.

Figure 20:
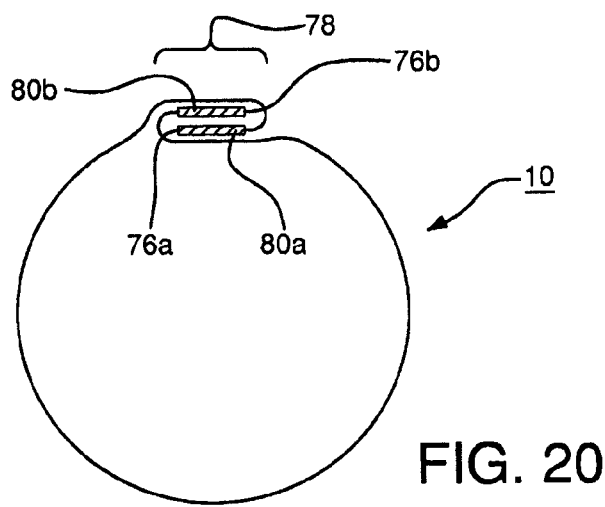
FIG. 20 is a cross-section view of another embodiment of a sheath of the present invention comprising a sheet of material that is formed into a tubular construct by interlocking pleats formed on edges of the sheet.

As the term "pleat" is used with respect the present invention, it refers to any fold or multiple folds in the sheath material that reduces the effective diameter of the sheath. In the preferred embodiment, each pleat comprises two folds that cause the sheath material to double back on itself. Alternatively, as is explained below, the pleat may comprise a single fold or multiple folds along an edge of a sheet of material, which may be interlocked, for instance as shown in FIG. 20. A pleat may also be formed through a rolling, twisting, or accordion folding of a section of material or similarly storing material for later un-pleating during deployment.

The sheath 10 everts over itself at a fold 36 at one end, in this embodiment at the distal end. As is explained below, the fold 36 may be oriented at either the distal end or the proximal end of the device, or anywhere in between.

In order to actuate the deployment line 26, medical personnel will unscrew the deployment knob 30 and pull on the knob and connected deployment line to cause the sheath to progressively withdraw off of the contained device. As the exterior segment of the sheath is withdrawn, the fold 36 will progress down the length of the contained device, steadily everting the interior segment 22 so that it becomes the exterior segment 20. In the process of everting, the pleat 32 will wrap around the fold 36 and open up. In this manner, the un-pleated exterior segment 20 will always remain at a larger effective diameter than the pleated interior segment 22 of the sheath. As a result, the larger diameter exterior segment 20 slides easily over the interior segment 22 and is readily removed with minimal friction between the two layers.

Figure 2:
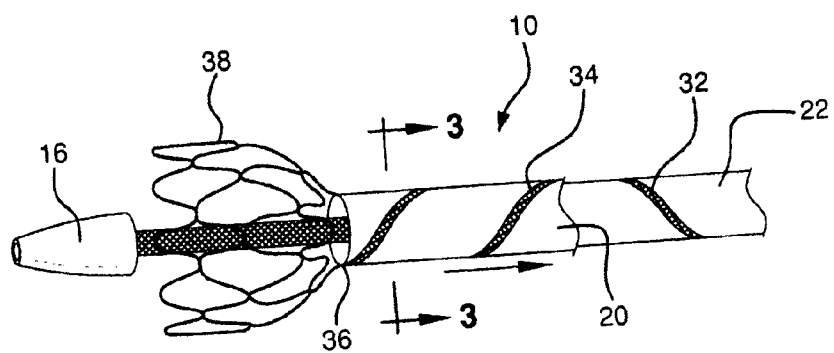
FIG. 2 is an enlarged perspective view of a distal end of a delivery catheter showing an everting pleated sheath of the present invention being withdrawn, progressively releasing a self-expanding stent contained therein.

The process of device delivery can be better seen in FIG. 2. In this embodiment, the interior segment 22 with its reinforced pleats 32 is shown exposed in cut-away. As the larger diameter exterior segment 20 is withdrawn, the pleats 32 open up along fold 36. Seen along the length of the exterior segment 20 are the strips of reinforcement material 34, now merely attached to the sheath 10 and no longer defining a pleat. As the sheath 10 is withdrawn in this manner, a constrained self-expanding stent 38 is progressively deployed from this embodiment.

Figure 3:
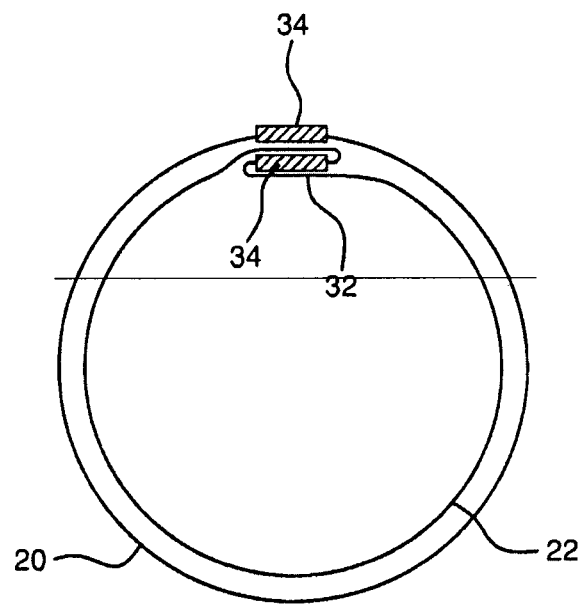
FIG. 3 is a cross-section view along line 3-3 of FIG. 2, showing only the pleated sheath component of the present invention.

As can be seen in the cross-section illustration of FIG. 3, the coaxial interior segment 22 and pleat 32 and reinforcement material 34 are shown within the larger diameter exterior segment 20 having only un-pleated reinforcement material 34.

Figure 4:
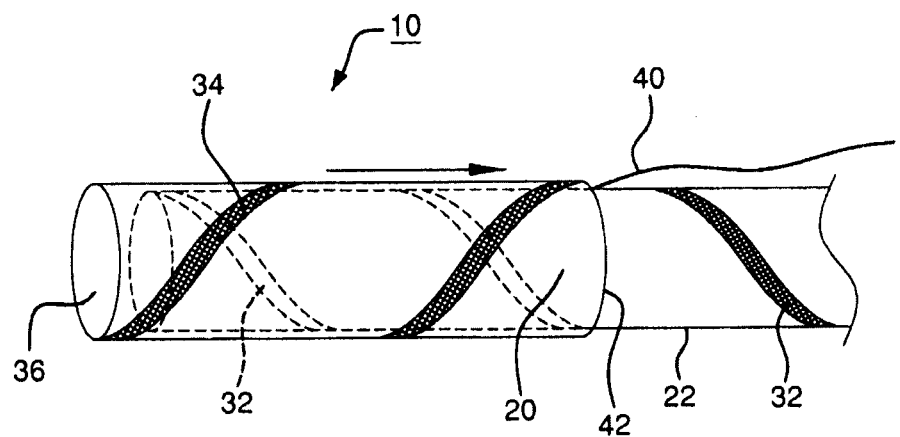
FIG. 4 is a perspective view of a portion of an everting pleated sheath of the present invention, showing the pleat unfolding during eversion of the sheath, the sheath being actuated by a deployment line.

FIG. 4 shows the process of un-pleating with the contained pleats 32 shown in phantom and the un-pleated reinforcement material 34 shown exposed along the exterior segment 20. Again, transition occurs along fold 36. In this embodiment a deployment line 40 is connected to one end 42 of the exterior segment 20. Tension on the deployment line 42 actuates the sheath 10.

Figure 5:
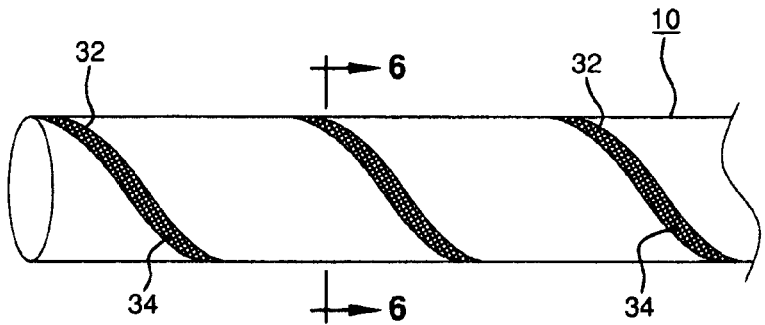
FIG. 5 is a perspective view of another embodiment of a pleated sheath of the present invention comprising a single layer.
Figure 7:
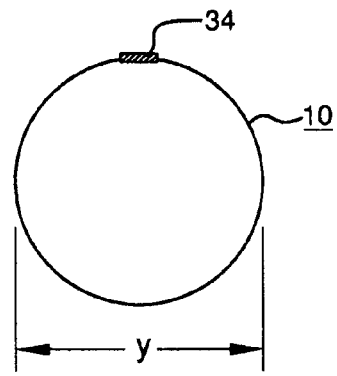
FIG. 7 is a cross-section view of the sheath of FIG. 5 following opening of the pleat, the sheath being of a greater effective diameter than the pleated orientation shown in FIG. 6.
Figure 6:
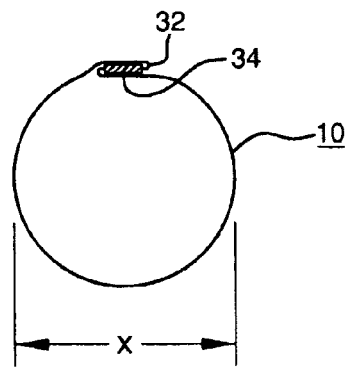
FIG. 6 is a cross-section view along line 6-6 of the sheath of FIG. 5.

FIG. 5 illustrates another embodiment of the present invention comprising a single layer sheath 10. The helically formed pleat 32 again includes a strip of reinforcement material 34. As can be seen in the cross-section of FIG. 6, the pleat 32 causes the sheath 10 to have a given diameter of x. Once the pleat 32 is released, as is shown in FIG. 7, the diameter of the sheath 10 enlarges to increased diameter of y.

With respect to single layer embodiments of the present invention, there are a variety of methods through which the sheath can be used. First, the pleats of the present invention are preferably stable without a constraining force. For instance, a sufficiently rigid pleat with sufficient helical angle will be inherently stable and will remain in place even without an external constraint. Alternatively, a variety of constraints can be provided to help retain the pleats in position. For instance, the single layer sheath may be formed and then everted over itself, either partially or entirely, and then employed in the manner described above. The everted portion of the sheath will maintain the pleats in their folded configuration until the device is ready for deployment. In another embodiment, the single layer sheath may be contained in another tubular structure to maintain the pleats in a folded configuration, such as through use of another sheath, a closely fitted catheter tube, or similar structure. In still another embodiment, the pleats can be joined to the sheath, such as through use of an adhesive, an adhered tape, a wrapped tape, a wrapped thread, or similar means, that will hold the pleats in position until the device is ready for deployment. A further method of deployment of a single layer sheath may include tensioning from the proximal end of the pleated tube (that is, the end closest to the clinician). When sufficient tension is applied, the pleat will unfold and the tube will increase diametrically allowing it to be translated relative to the device.

Figure 8:
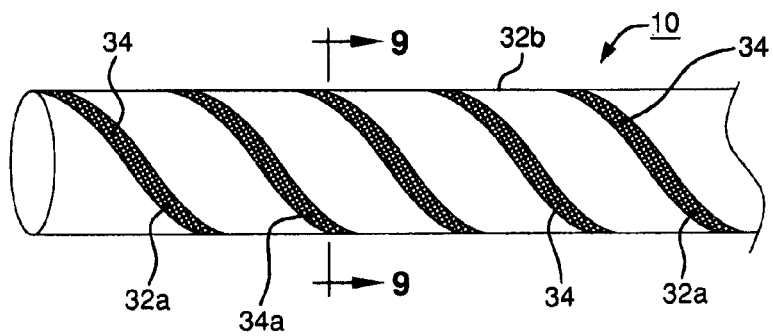
FIG. 8 is a perspective view of still another embodiment of a pleated sheath of the present invention comprising a single layer and having two pleats provided therein.
Figure 9:
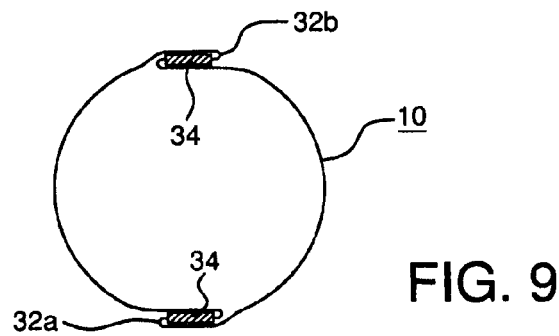
FIG. 9 is a cross-section view along line 9-9 of FIG. 8.

Illustrated in FIGS. 8 and 9 is a still another embodiment of a pleated sheath 10 of the present invention. In this embodiment, the sheath 10 comprises a single layer and includes two pleats 32a, 32b therein. The pleats may be evenly aligned on opposite sides of the sheath 10, as shown, or may be placed in other orientations. It should be understood that depending on desired deployment specifications, the present invention can be practiced with one, two, three, four, five or more pleats along part or all of the sheath length.

Figure 10:
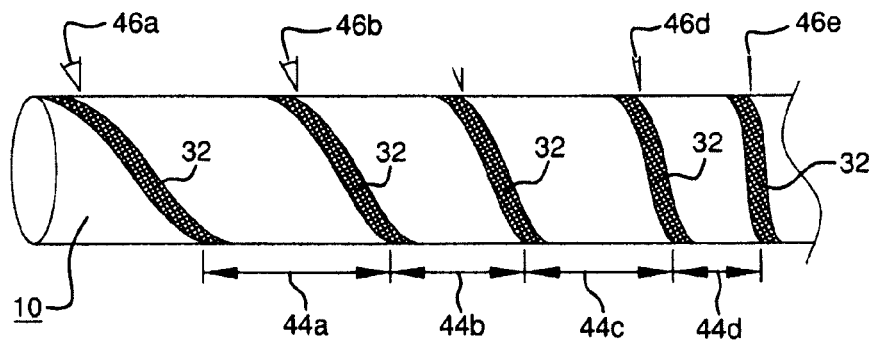
FIG. 10 is a perspective view of another embodiment of a sheath of the present invention wherein the spacing and pitch of the element that will define the pleat is changed along the length of the sheath in order to provide a variable diameter along the sheath length after the pleat is formed.

FIG. 10 illustrates another embodiment of a sheath 10 of the present invention wherein the spacing 44a, 44b, 44c, 44d between pleating elements 32 varies along the length of the sheath 10. Likewise, the pitch 46a, 46b, 46c, 46d, 46e of the helical wraps of the pleating elements 32 also varies along the length of the sheath 10. Each of these properties can be adjusted, independently or in cooperation, in device design so as to provide varying diameters along the length of the sheath after pleating. Diameter may be varied along the length of the sheath to accommodate non-cylindrical device profiles and/or produce variable sheath removal properties.

Figure 11:
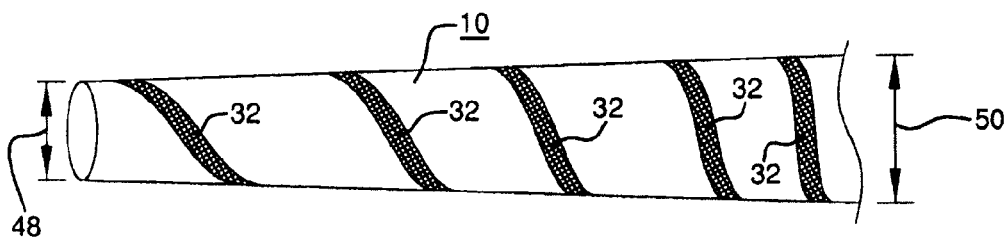
FIG. 11 is a perspective view of the sheath of FIG. 10 after it has been pleated.

FIG. 11 depicts the sheath of FIG. 10 after it has been pleated. In this instance, the sheath and contained device provide a tapered profile, with the distal end 48 being a smaller diameter than the proximal end 50.

Figure 12:
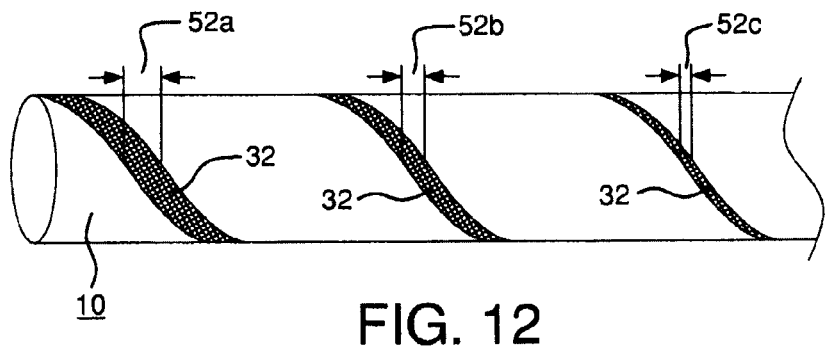
FIG. 12 is a perspective view of another embodiment of a sheath of the present invention wherein the width of the element that will define the pleat is changed along the length of the sheath.

In the embodiment of FIG. 12, width 52a, 52b, 52c of the pleating element is changed along the length of the sheath 10. Again, by changing pleat width, diameter can be varied along the length of the sheath to accommodate non-cylindrical device profiles and/or produce variable sheath removal properties. For instance, by making the pleating elements progressively narrower along the length of the device as shown, the pleated sheath can be formed with a variable diameter, producing either greater or lesser friction (depending on the direction of deployment) as the sheath is deployed along its length—making it either initially easier or more difficult to deploy the sheath.

Figure 13:
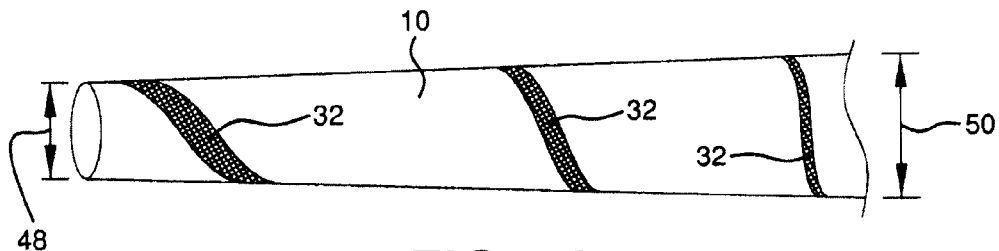
FIG. 13 is a perspective view of the sheath of FIG. 12 after it has been pleated.

FIG. 13 depicts the sheath of FIG. 12 after it has been pleated. In this instance, the sheath and contained device provide a tapered profile, with the distal end 48 being a smaller diameter than the proximal end 50.

Figure 14:
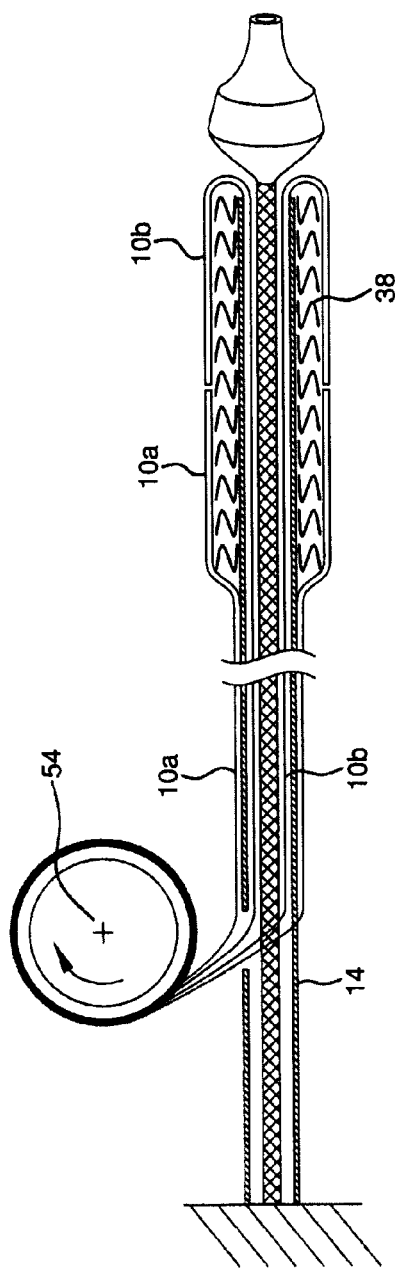
FIG. 14 is a longitudinal cross-section view of a delivery catheter incorporating a pair of sheaths of the present invention and containing a compacted device, the pair of sheaths being oriented to withdraw from the device in opposite directions from a point midway along the device.

Shown in FIG. 14 is a delivery catheter incorporating a pair of sheaths of the present invention and containing a compacted device 38, the pair of sheaths 10a, 10b being oriented to withdraw from a compacted device 38 in opposite directions from a point midway along the device. Proximal sheath 10a runs along catheter shaft 14 to an actuation mechanism 54. Distal sheath 10b is withdrawn in the opposite direction (that is, towards the distal end of the catheter 14) and is inverted into the catheter shaft 14. The distal sheath 10b is likewise controlled by actuation mechanism 54.

By actuating the two sheaths in this embodiment, the two sheaths 10a, 10b are withdrawn simultaneously from the compacted device 38 to allow it to deploy from its middle outward. Such deployment may be useful in those instances where very rapid device deployment is sought and/or where it is desirable to minimize the effect of high volume of blood flow upon the device prior to full deployment (for instance, when a device is deployed in the aorta and it is desirous to have the upstream end of the device deploy last so as to avoid a "windsock" effect in the high-volume blood flow which may misalign device positioning).

Figure 15:
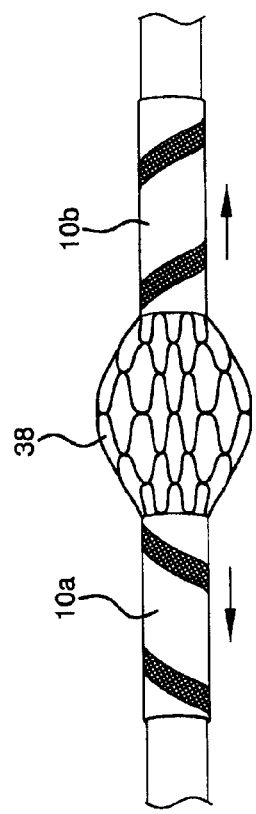
FIG. 15 is an enlarged perspective view showing a stent-graft device being deployed from a midpoint by removing two sheaths of the present invention in opposite directions.

FIG. 15 illustrates how a stent-graft device 38 can be deployed from its midpoint by removing two sheaths 10a, 10b. This deployment method would be preferred for placing a stent-graft device in a thoracic aorta or the like.

It should be understood that for some applications it may be preferred to actuate each of the sheaths 10a, 10b independently of each other so that only part of the device is deployed at any given time. This can be readily accomplished by providing separate actuation mechanisms for each of the sheaths. It should be further appreciated that with respect to all of the embodiments of the present invention discussed herein it may be desirable to have sheath deployment occur either from the distal end of the catheter back or from the proximal end of the catheter forward, or with two or more deployment sheaths moving in opposite directions, as illustrated in the embodiments of FIGS. 14 and 15.

Figure 16A:
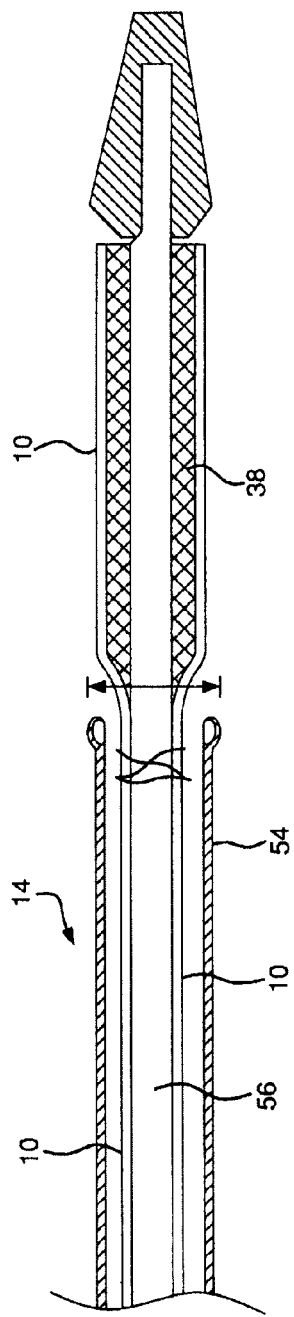
FIG. 16A is a longitudinal cross-section view of a distal portion of a catheter utilizing a sheath of the present invention, showing another embodiment of apparatus to remove the sheath.
Figure 16B:
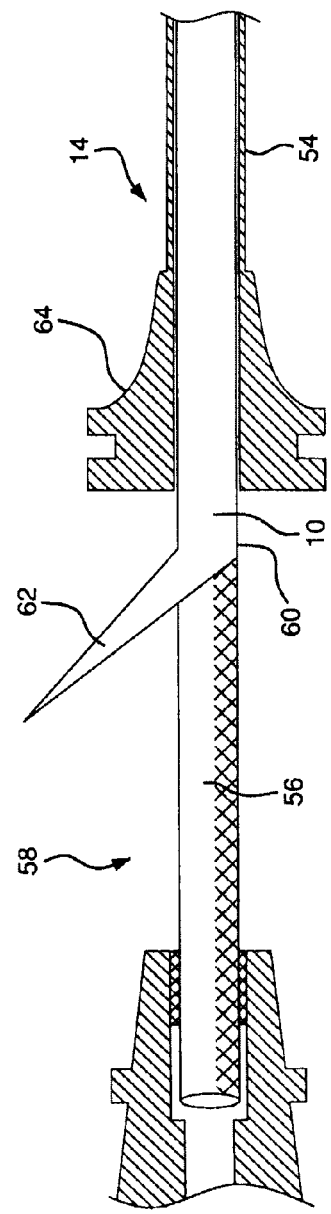
FIG. 16B is a longitudinal cross-section view of a proximal portion the catheter shaft of FIG. 16A.

FIGS. 16A and 16B illustrate a deployment mechanism similar to the one shown in FIG. 14. In this embodiment, a single everted sheath 10 is provided constraining a device 38. The sheath 10 extends proximally within an outer casing 54 of catheter shaft 14, coaxially surrounding inner catheter shaft 56. The sheath 10 extends to the proximal end 58 of the catheter 14, where it can be actuated by a user. In this embodiment, the sheath 10 is constructed from a material that will split longitudinally, such as through a pre-formed longitudinal line of perforations or similar weakening means 60, so that the sheath 10 can be removed from the inner shaft 56 by applying tension to tail 62, as is shown in FIG. 16B. A strain relief 64 may be provided on the distal end of the outer casing 54 to assist in handling of the catheter 14 during placement and deployment.

Another deployment mechanism that may be used with the present invention is shown in FIGS. 17A and 17B. In this embodiment, a dual lumen catheter 14 is provided, having a lumen 66 for housing inner shaft 56 and a lumen 68 designed to accept a deployment line 40. The deployment line 40 is integral with or attached to the sheath 10. The line 40 is actuated to cause the sheath 10 to withdraw in the manner previously described.

The preferred sheath of the present invention for containing and deploying a self-expanding stent or stent-graft for vascular applications will be constructed of a thin, lubricous polymer material, such as an ePTFE multi-layer laminated film tube, with a thickness of 0.03 to 0.3 mm, and more preferably 0.05 to 0.12 mm. In light of the present description, it should be evident that the tube of the present invention is preferably as thin as possible while having strength properties that will withstand loading forces and effectively constrain the device until it is deployed.

Figure 18:
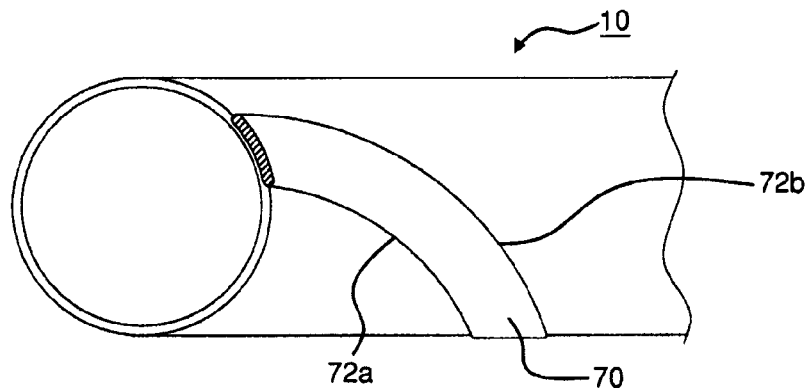
FIG. 18 is a three-quarter isometric view of another single-layer sheath of the present invention including additional thickness of material along a portion of a monolithic structure to provide pleat reinforcement.
Figure 19:
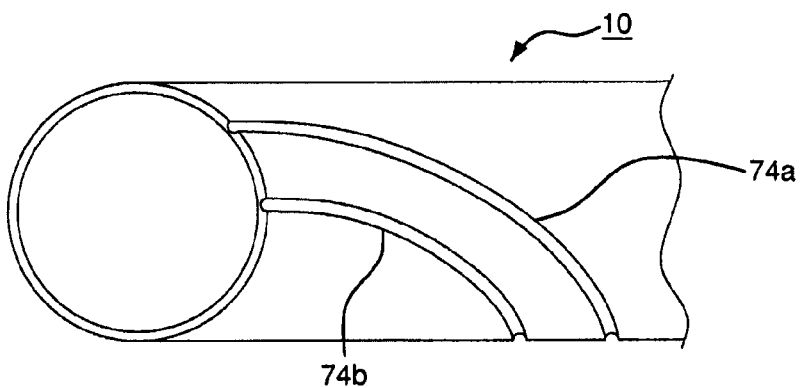
FIG. 19 is a three-quarter isometric view of another single-layer sheath of the present invention including surface treatment of the sheath in order to provide a defined pleat hinge line.

Still other embodiments of pleats that may be employed in the present invention are illustrated in FIGS. 18 through 20. FIG. 18 illustrates a pleat reinforcement 70 that is formed from the same material as the sheath 10 itself. Such reinforcement 70 is achieved by providing a layer of additional material along a portion of the sheath circumference so as to provide defined fold lines 72a, 72b on either side of the raised reinforcement 70. This construct may be formed by extruding or otherwise adding additional material in the defined manner on the sheath and/or removing material from, or densifying material on, the remainder of the sheath 10 in order to leave a pleat reinforcement 70 of increased dimension. A similar effect may be achieved by densifying the reinforcement area in order to establish fold-resistance.

FIG. 19 illustrates another approach to achieve predictable sheath folding. In this embodiment the sheath 10 has been treated to provide one or more defined pleat hinge lines 74a, 74b. Each hinge line 74 may be formed through any of a variety of surface treatment means, including through mechanical methods (e.g., cutting, scoring, densification, etc.), through extrusion or other material manufacture steps, or through thermal processing (e.g., through heat or laser treatment), or some combination of such various methods. The pleated configuration of the sheath 10 is folded along these hinge lines 74.

It should be evident that with respect to the embodiments of both FIG. 18 and FIG. 19, the desired result is achieved by forming a pleat region with sufficient relative stiffness and/or thickness to resist folding or otherwise to fold preferentially. Additionally, using these techniques the sheath can be provided with preferential folding properties without the need to add additional material to the sheath.

FIG. 20 illustrates still another method of forming a pleat in accordance with the present invention. In this embodiment the sheath 10 is formed from a sheet of material having two edges 76a, 76b. Each of these edges 76a, 76b can then be folded to form a pleat 78a, 78b with one or more folds. The edge pleats 76a, 76b can then be interlocked with one another, for instance as shown, to create a tubular structure that serves as the sheath 10 of the present invention. In this embodiment when the pleat 10 is opened, the edges 76 will separate from each other to provide the desired predictable enlargement of the present invention. One or both of the edges 76 can be provided with reinforcement 80a, 80b, such as through one of the methods previously described, in order to facilitate the formation and retention of the pleat 78.

It should be appreciated that in the everted embodiments of the present invention, in the final construct the exterior segment should have an inner diameter that is sufficiently greater than the outer diameter of the interior segment in order to minimize friction between the two segments. That is, in order to minimize interference between the interior segment and the exterior segment, the un-pleated exterior segment should enlarge enough so that its inner diameter comfortably clears the outer diameter of the pleated interior segment. It is preferred that the inner diameter of the exterior segment be 0.1 to 50% larger than the outer diameter of the interior segment, and more preferably 10 to 20% larger.

For example, to achieve these dimensions, a sheath with a wall thickness of about 0.08 mm and an un-pleated a inner diameter of about 2.1 mm will typically be provided with one or more pleats with a pleat width of 0.8 mm to create a pleated interior segment having a outer diameter of about 1.9 mm.

In the preferred embodiments of the present invention for the deployment of a self-expanding stent or stent-graft, pleats are provided with a width of 0.3 to 2.0 mm, and more preferably with a width range of 0.6 to 1.3 mm. Pleats will typically be oriented helically around the sheath, with a typical pitch angle of 30 to 75 degrees, and more preferably a pitch of 50 to 70 degrees.

The pleats are preferably reinforced with a strip or strips of relatively fold-resistant material, such as polyimide film, with a thickness of 0.01 to 0.08 mm, and more preferably 0.02 to 0.05 mm. The reinforcement material is encapsulated between layers of a laminated sheath, adhered using an adhesive such as FEP or similar material.

While the preferred sheath of the present invention includes one or more pleats helically oriented along part or all of the longitudinal length of the sheath, it should be appreciated that other pleat orientations as likewise contemplated by the present invention. For example, so long as they are adequately constrained or adhered the pleat or pleats may be arranged essentially parallel to the axis of the device. Further, for some applications multiple discontinuous pleats may be provided to achieve suitable deployment properties. Additionally, for some applications it may be desirable to provide pleats along at least a portion of both the interior segment and the exterior segment of the sheath.

The sheath of the present invention has been determined to vastly reduce the amount of tension required to deploy a device. In this regard, deployment tensions are typically on the order of 50-150 grams It should be noted that the present invention may be scaled to virtually any dimensions.

EXAMPLE

Without intending to limit the scope of the present invention, the following example illustrates one embodiment of how the present invention may be practiced.

Sheath Tube Construct:

(1) A 1" (25.4 mm) wide strip of expanded polytetrafluoroethylene (ePTFE) film (having predominantly longitudinally oriented strength, film thickness of approximately 0.006 mm and break strength of approximately 0.8 kg/cm width) was "cigarette" wrapped on a 0.11" (2.8 mm) diameter×40 cm long mandrel. The film structure was orientation parallel to mandrel axis so that the film was stronger parallel to the mandrel's longitudinal axis.

(2) A second layer of 0.4" (10 mm) wide ePTFE/FEP laminate film (predominantly longitudinally oriented strength, total film thickness of approximately 0.003 mm, FEP thickness of approximately 0.001 mm and break strength of approximately 0.7 kg/cm width) was then helically overwrapped around the first film layer with a single pass at a 0.2" (5 mm) pitch, to create a double thickness of the second film layer. The oriented film structure of the second layer was aligned in the helical direction around the mandrel.

(3) A 0.035" (0.89 mm) wide×0.001" (0.025 mm) thick strip of polyimide was wrapped over the second film layer at a pitch of 0.375" (9.5 mm).

(4) A second pass of the second layer of film was wrapped over the polyimide in a direction opposing the previous pass of the second layer of film.

(5) The wrapped tube was thermally processed on-mandrel at a temperature of 380° C. for 8 minutes, after which the tube (approximately 25 cm in length) was stripped from the mandrel.

(6) The tube was helically pleated by manually flipping the polyimide strip 180°. Approximately 11 cm of the tube was pleated with the pleat originating at one end of the tube, open side of the pleat facing away from the un-pleated section. Pleated inside diameter of the tube was approximately 0.095" (2.4 mm) with the helical pleat having a pitch of about 0.23" (5.8 mm). Approximately 14 cm of the tube was left un-pleated.

Loading:

(1) Traction lines were attached to each of the six leading apices on an 8 mm×10 cm GORE VIABIL® endoprosthesis device (available from W. L. Gore & Associates, Inc., Flagstaff, Ariz.). A Pebax® coated, braided stainless steel shaft (approximately 0.038" (0.97 mm) I.D., 0.045" (1.1 mm O.D.) was positioned in the lumen of the device.

(2) A long stainless steel nozzle (approximately 100 mm length, 0.095" (2.4 mm) outer diameter, 0.088" (2.2 mm) inner diameter) was fixed to the small end of a stainless steel loading funnel. The funnel was sized with a wide opening of approximately 14 mm diameter, a small funnel opening of approximately 2.2 mm diameter and a straight taper approximately 34 mm in length.

(3) The pleated end of the tube was positioned on the O.D. of the nozzle with the pleat extending approximately 5 mm beyond the end of the nozzle. The open side of the pleat was facing the funnel end of the nozzle.

(4) The endoprosthesis was compressed by pulling it through the funnel and attached nozzle, via the attached traction lines. As the device exited the nozzle, the pleated tube was fed from the O.D. of the nozzle onto the compressed device, constraining the device at the pleated diameter.

(5) With the entire device pulled through the nozzle and subsequently constrained in the pleated tube, the un-pleated section of the tube was everted over the device.

Deployment:

(1) Deployment of the device was accomplished by tensioning and displacing the outer, un-pleated, section of the tube relative to the device, releasing it from its constrained state.

(2) As the tube is everted, the pleat opens up or unfolds at the point of eversion, allowing the un-pleated outer layer of the tube to translate relative to the pleated inner layer without interference.

It was determined that this delivery tube could be deployed with significantly less deployment line tension than a comparably constructed everted tube that did not include pleats. A conventional tensile test was conducted on an un-pleated everting sheath and a pleated everting sheath of the present invention, the sheaths being otherwise comparable in material and construction, using an INSTRON Tensile Tester employing a crosshead speed of 400 mm/min.

Figure 21:
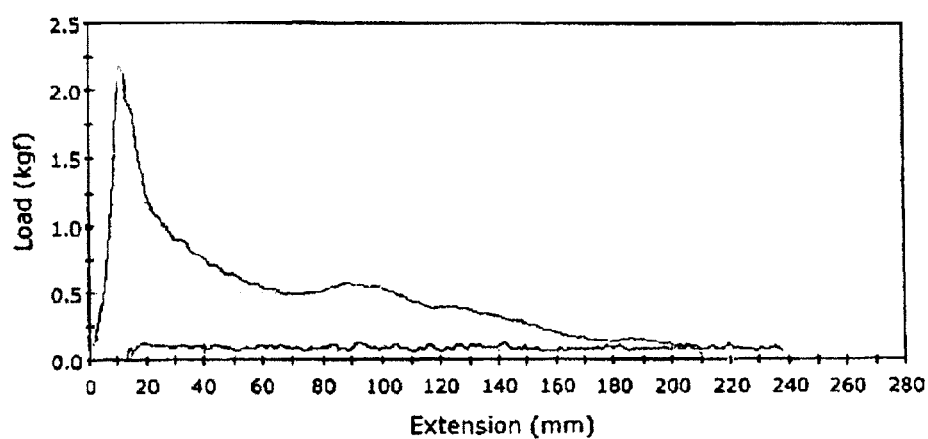
FIG. 21 is a graphical illustration of load encountered by a development line of the present invention at various points in time.

With reference to FIG. 21, tension required to deploy the pleated sheath of the present invention was consistent throughout the deployment with a peak of approximately 0.074 kg. Tension required to deploy the conventional everting sheath without pleats was approximately 2.2 kg initially, reducing to approximately 0.50 kg midway through the deployment. FIG. 21 is a graphical representation of the load encountered by the development line at various points in time, wherein the upper plot shows the load encountered by a deployment line attached to the conventional un-pleated everting sheath during device deployment, and the lower plot shows the load encountered by a deployment line attached to the pleated everting sheath of the present invention during device deployment.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A medical device delivery system comprising
a tubular constraining sheath, having a length, mounted about and containing a medical device;
wherein said tubular constraining sheath includes at least one pleat oriented along at least a portion of the length, wherein said pleat is stable when constraining a medical device;
wherein at least a portion of said tubular constraining sheath is everted over itself prior to deployment of said medical device to form an everted portion having a length; and
wherein when tension is applied to the everted portion, the length of the everted portion increases, the everted portion slides along the length of the device, and the pleat progressively opens to provide an enlarged diameter to the everted portion.

2. The medical device delivery system of claim 1 wherein the pleat is oriented helically along at least a portion of the length of the sheath.

3. The medical device delivery system of claim 1 wherein the sheath includes an aid in forming said pleat.

4. The medical device delivery system of claim 1 wherein a portion of the pleat is reinforced.

5. The medical device delivery system of claim 4 wherein the pleat is reinforced with a reinforcing material.

6. The medical device delivery system of claim 5 wherein the reinforcing material comprises a polymer strip attached to the sheath.

7. The medical device delivery system of claim 1 wherein the sheath comprises expanded polytetrafluoroethylene.

8. The medical device delivery system of claim 7 wherein the sheath comprises a tube of multiple layers of expanded polytetrafluoroethylene film.

9. The medical device delivery system of claim 1 wherein the medical device is an endoprosthesis.

10. The medical device delivery system of claim 9 wherein the endoprosthesis is a self-expanding device.

11. A medical device deployment system comprising
a medical device having a length;
a constraining sheath mounted around the medical device along at least a portion of its length,
wherein prior to deployment the sheath is at least partially everted over itself to form an interior segment and an exterior segment;
wherein at least a portion of the interior segment of the constraining sheath includes a helically oriented pleat, wherein said pleat is stable when constraining said medical device; and
wherein deployment occurs by applying tension to the exterior segment of the sheath to evert the interior segment and progressively reorient it into the exterior segment with the pleat progressively opening as the sheath everts creating an unpleated exterior segment and a pleated interior segment.

12. The medical device deployment system of claim 11 wherein the un-pleated exterior segment is of a sufficiently greater diameter than the pleated interior segment so as to reduce frictional contact between the interior segment and the exterior segment during deployment.

13. The medical device deployment system of claim 11 wherein a portion of the pleat is reinforced with a reinforcing material.

14. The medical device deployment system of claim 13 wherein the reinforcing material comprises a polymer strip attached to the sheath.

15. The medical device deployment system of claim 11 wherein the sheath comprises expanded polytetrafluoroethylene.

16. The medical device deployment system of claim 15 wherein the sheath comprises a tube of multiple layers of expanded polytetrafluoroethylene film.

17. The medical device delivery system of claim 11 wherein the medical device is an endoprosthesis.

18. The medical device delivery system of claim 17 wherein the endoprosthesis is a self-expanding device.

19. A delivery and deployment system for an endoprosthesis, comprising:
an endoprosthesis having a distal end, a proximal end, a first, smaller compacted diameter for insertion into a body conduit and a second, larger deployed diameter, said endoprosthesis provided at the first, smaller compacted diameter; and a constraining sheath wherein a first length portion of said sheath is fitted around the compacted endoprosthesis and extends along a length of the endoprosthesis and a second length portion that is everted back over the first length portion, wherein at least the first length portion of the constraining sheath includes a helically oriented fold, wherein said fold is stable when constraining said endoprosthesis, and wherein when tension is applied to the second length portion, a length of the second length portion increases, the second length portion slides along the length of the device, and the helically oriented fold progressively opens to provide an enlarged diameter to the second length portion.

* * * * *